United States Patent
Schon

(10) Patent No.: US 9,156,769 B2
(45) Date of Patent: Oct. 13, 2015

(54) METHOD OF RECOVERING CARBOXYLIC ACIDS FROM DILUTE AQUEOUS STREAMS

(71) Applicant: Arkema Inc., King of Prussia, PA (US)

(72) Inventor: Steven G. Schon, Strafford, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 14/222,967

(22) Filed: Mar. 24, 2014

(65) Prior Publication Data

US 2014/0221686 A1 Aug. 7, 2014

Related U.S. Application Data

(63) Continuation-in-part of application No. 13/123,823, filed as application No. PCT/US2009/057942 on Sep. 23, 2009, now abandoned.

(60) Provisional application No. 61/105,527, filed on Oct. 15, 2008.

(51) Int. Cl.
  C07C 51/48 (2006.01)
  C07C 45/80 (2006.01)

(52) U.S. Cl.
  CPC ............... *C07C 51/48* (2013.01); *C07C 45/80* (2013.01)

(58) Field of Classification Search
  None
  See application file for complete search history.

(56) References Cited

U.S. PATENT DOCUMENTS

| | | | |
|---|---|---|---|
| 3,868,175 A | 2/1975 | Duembgen et al. | |
| 3,868,417 A | 2/1975 | Duembgen et al. | |
| 4,447,643 A | 5/1984 | Feldman | |
| 5,399,751 A | 3/1995 | Gentry et al. | |
| 5,492,625 A | 2/1996 | Wytcherley et al. | |
| 6,639,106 B1 * | 10/2003 | Elder et al. | 562/600 |
| 6,737,546 B2 | 5/2004 | Wagner et al. | |
| 6,995,282 B1 | 2/2006 | Fauconet et al. | |
| 2002/0037563 A1 | 3/2002 | Staley | |
| 2003/0092937 A1 | 5/2003 | Wagner et al. | |
| 2005/0279623 A1 | 12/2005 | Speidel | |

FOREIGN PATENT DOCUMENTS

| CA | 2 282 492 A1 | 9/1998 |
|---|---|---|
| CA | 2282492 * | 9/1998 |

OTHER PUBLICATIONS

"Propylene" in Kirk-Othmer Encyclopedia of Chemical Technology, Calamur et al., Copyright © 2001 by John Wiley & Sons, Inc., Published Online: Dec. 2, 2005.*

* cited by examiner

*Primary Examiner* — Karl J Puttlitz
(74) *Attorney, Agent, or Firm* — Steven D. Boyd

(57) ABSTRACT

Improvement in separating lower carboxylic acids from aqueous streams via liquid-liquid extraction with pressurized liquefied propylene and/or propane, wherein carboxylic acid is transferred from the aqueous phase into the liquid solvent phase (extract). The extracted carboxylic acids are recovered as a liquid concentrate by evaporating off the propylene and/or propane solvent from the extract at mild temperatures.

8 Claims, 7 Drawing Sheets

LLE Data for the Ternary System
Water + Acrylic Acid (AA) + Propylene

METHOD OF RECOVERING CARBOXYLIC ACIDS FROM DILUTE AQUEOUS STREAMS

This application is a continuation-in-part of U.S. application Ser. No. 13/123,823 filed Apr. 12, 2011 which claimed priority to International Application Ser. No. PCT/US09/57942 filed on Sep. 23, 2009 which claims priority to U.S. Provisional Application Ser. No. 61/105,527, filed Oct. 15, 2008, all of which are incorporated herein by reference.

BACKGROUND OF THE INVENTION

1. Field of the Invention

The present invention relates to a method for recovering carboxylic acids from dilute aqueous streams via liquid-liquid extraction with a solvent comprising pressurized liquefied propylene and/or propane. More particularly, the present invention relates to a method for recovering acrylic acid from dilute acid water streams in processes for the manufacture of acrolein or acrylic acid.

2. Discussion of the Prior Art

Both acrolein and acrylic Acid (AA) are conventionally produced by gas-phase catalytic oxidation of propylene. There are also reports in the patent and open literature that with suitable catalysts, propane can be used as a feedstock in lieu of propylene.

In acrolein manufacture, the reaction is typically carried out in a single-stage reactor, optimized to selectively oxidize propylene or propane to acrolein, with a minimum of byproducts. However, some over-oxidation occurs resulting in the production of AA as well. In AA manufacture, the reaction is typically rallied out in two stages, oxidizing propylene or propane to acrolein in the first stage (as in acrolein manufacture), and then further oxidizing the acrolein to AA in the second stage.

In both acrolein and AA manufacture, AA is first separated from the gas phase reactor effluent by absorption into water, resulting in a dilute aqueous AA stream that also contains water-soluble, medium- and higher-boiling reaction byproduct impurities such as acetone, allyl alcohol, acetic acid, propionic acid, and maleic acid.

In AA manufacture, the aqueous AA stream leaving the absorber typically contains less than 40-65% AA. This crude aqueous AA stream is sent to a purification system which typically involves a series of energy-intensive distillation columns. Because of the relatively high water content, and the fact that AA forms azeotropes with water and other reaction impurities, the AA purification system is complex and energy intensive.

In acrolein manufacture, the aqueous AA stream leaving the absorber typically contains less than 10% AA; at standalone manufacturing sites, it is handled as a waste. Although dilute in AA, the concentrations are sufficiently high to make it impractical to treat the wastewater by relatively low-cost means such as biological treatment or wet-air oxidation. Thus, the AA wastewater is typically sent to an incinerator. Operating the incinerator requires a large amount of fuel owing to the large amount of water present, relative to the AA. Thus, handling and incineration of the dilute AA stream represents a significant operating expense in the manufacture of acrolein. While in principle the aqueous AA could be transported to an off-site AA manufacturing facility for recovery of the AA, the dilute AA concentration makes transportation costs prohibitive.

In the case of acrolein manufacture, it would be desirable to separate and recover AA from the dilute wastewater stream, yielding an AA concentrate, and an AA-depleted wastewater. The AA concentrated could be transported economically to an off-site AA manufacturing facility, for purification of the AA into a commercially valuable product. The AA-depleted wastewater may have a sufficiently low concentration of residual organic compounds, so that it can be feasibly treated by less expensive means than incineration, e.g. biological wastewater treatment or wet-air oxidation.

In case of AA manufacture, it would be desirable to separate the AA from the water in crude AA exiting the absorber. Reducing the water loading in the crude AA sent to purification reduces the energy requirements and costs in the distillation train.

The prior art describes various extraction-based processes for separating carboxylic acids, especially AA, from aqueous streams. However, most of these involve solvents are liquid at ambient temperatures, and often involve solvents whose boiling points are higher than that of water or water-AA mixtures. This makes it cumbersome to recover the solvent in at sufficiently high purity to allow recycle to extraction without causing a build-up of undesirable impurities. The use of these alternative solvents has the further disadvantage of requiring the handling of additional materials in the manufacture of acrolein or AA.

Alternative solvents that are more volatile than AA do not have a high enough relative volatility to afford a clean separation in a single-stage flash from either AA or some of the other impurities (propylene oxidation reaction byproducts) that co-extract with the AA. This requires that a more complex purification process (e.g. fractional distillation) be used to purify the solvent for recycle. Without purification, the solvent would accumulate impurities or AA, limiting the efficiency of the extraction step.

In order to avoid taking the carboxylic acids as bottom streams, the alternative is to use solvents which are less volatile, i.e. high-boiling, than the carboxylic acids, as the carboxylic acids are boiled overhead, and the solvent generally is taken as the bottoms streams. This can lead to increased polymerization or fouling due to the relatively high temperatures required to boil-up AA (even under vacuum), as well as the propensity of uninhibited AA vapors to polymerize when re-condensing. The fouling tendency can be mitigated by reducing the pressure of the distillations and for the addition of polymerization inhibitors to the distillation system. This is well known in the art.

Many AA extraction solvents described in the prior art are somewhat polar materials, rather than simple non-polar hydrocarbons. Consequently, the AA solutions in the polar solvents tend to form azeotropes, which further complicates the downstream purification of AA.

It is desirable to be able to extract AA without using additional chemicals (e.g. solvents) that are not otherwise required in the manufacturing process; i.e. to use only materials in the synthesis process as the extraction agent, as this avoids the logistics, costs, hazards, permitting, and material handling issues associated with introducing a new chemical into a manufacturing facility.

Prior art related to Acrylic Acid separation using solvent extraction includes the following:

U.S. Pat. No. 6,995,282 discloses the use of at least one heavy hydrophobic absorption solvent having a boiling point at atmospheric pressure of greater than 200° C. carboxylic acids from aqueous solutions.

U.S. Pat. No. 3,868,417 discloses carboxylic esters of melting point less than 30° C. and boiling point at normal pressure greater than 160° C. at elevated temperature and a pressure of 0.5 to 5 bars such as methyl, ethyl, n-butyl, isooctyl-2-ethylhexyl and/or octyl esters of oleic acid, adipic acid and/or phthalic acid carboxylic acids from aqueous solutions.

U.S. Pat. No. 3,868,175 discloses the use of a dual solvent consisting of the first component capable of forming an azeotropic mixture with acrylic acid, acetic acid and water and the second component having a lower boiling point than that of acetic acid. The first component used is in an azeotropic relation with acrylic acid and acetic acid, and includes, for example, ethyl benzene, o-xylene, m-xylene, p-xylene, and octane. The second component has a boiling point lower than that of acetic acid, and includes, for example, methylethylketone, methyl acetate, and ethyl acetate for recovering carboxylic acids such as acrylic acid from aqueous solutions.

U.S. Pat. No. 6,737,546 discloses of the use of an immiscible solvent comprising propyl acetate and a cyclohexane and an integrated sequence of distillations and phase separations to separate the desired product or products and recover for recycle organic components of the extraction solvent.

U.S. Pat. No. 5,399,751 discloses the use a solvent consisting essentially of mixed trialkylphosphine oxides for recovering carboxylic acids from aqueous solutions.

Canadian Patent Application CA 2 282 492, discloses the use of materials that can be converted into (meth)acrylic acid as the extracting agents for extracting methacylic or acrylic acids from aqueous solutions.

SUMMARY OF THE INVENTION

Carboxylic acids, especially acrylic acid (AA), are recovered from dilute aqueous mixtures by liquid-liquid extraction with pressurized liquefied propylene and/or propane, wherein carboxylic acid is transferred from the aqueous phase into the liquid solvent phase (extract). One or more polymerization inhibitors is added either to the liquefied solvent, or to the extract solution, to ensure that the extract contains inhibitors prior to concentration of the recovered carboxylic acid. The carboxylic acid is concentrated from the extract by boiling-off (evaporating) the propylene/propane solvent at mild temperatures; the solvent vapor can be condensed and re-used (all, or in part) in the extraction step, and/or used as a raw material in the process which generated the carboxylic acids. The concentration of the carboxylic acid may be carried out by means of one or more evaporators in series, or by means of distillation. The recovered carboxylic acid may be purified from the concentrate by means known to those skilled in the art of carboxylic acid processing; such means is outside the scope of the present invention. The extraction and/or the concentration steps may be carried out as either batch or continuous operations.

DETAILED DESCRIPTION OF THE INVENTION

Figure 1:
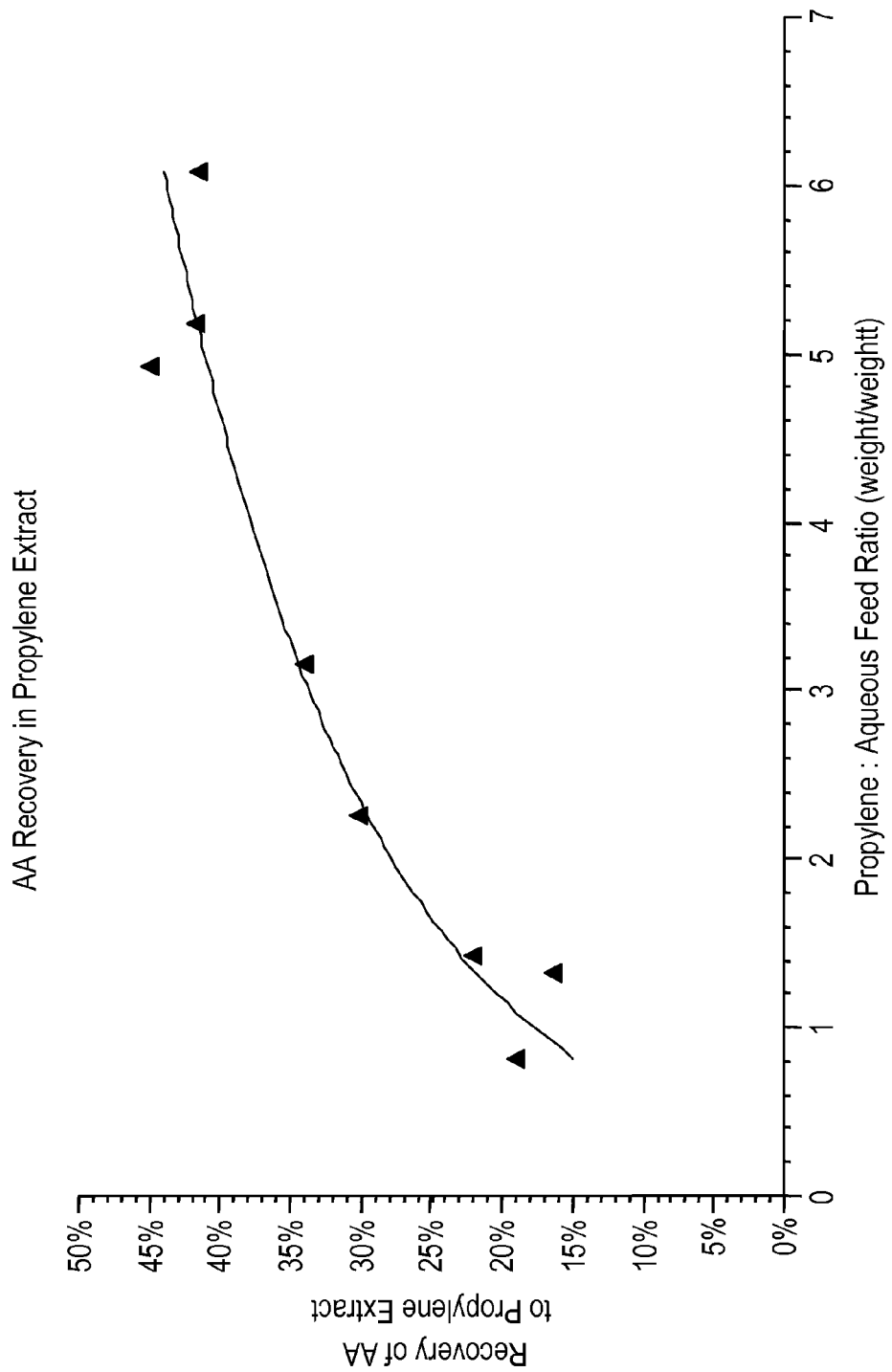
FIG. 1 is a plot of AA recovery versus Propylene:Aqueous Feed Ratio for Examples 1-1.

The present invention is directed towards a method to recover and concentrate C2 saturated and/or C3, and/or C4 saturated and/or unsaturated mono carboxylic acids, especially acrylic acid, from dilute aqueous solutions. More particularly, the present invention is directed toward a method to recover carboxylic acid from wastewater streams, as a concentrate that is compatible with established carboxylic acid purification systems. Further, the present invention uses as recovery agents chemicals that are normally used in the synthesis of the carboxylic acids. Further, the present invention is directed towards a method to maximize the water removal from aqueous C2 saturated and/or C3, and/or C4 saturated and/or unsaturated mono carboxylic acids, especially acrylic acid, to minimize the energy requirements for the downstream purification of the carboxylic acids. The method of the present invention achieves desired C2 saturated and/or C3, and/or C4 saturated and/or unsaturated mono carboxylic acid recovery and concentration at high overall recoveries of such carboxylic acids, i.e., minimizing losses to separation inefficiencies and formation of decomposition/degradation products.

In the method of the present invention C2 saturated and/or C3, and/or C4 saturated and/or unsaturated mono carboxylic acids, especially acrylic acid (AA), are recovered from dilute aqueous mixtures by liquid-liquid extraction with pressurized liquefied propylene and/or propane, wherein carboxylic acid is transferred from the aqueous phase into the liquid solvent phase (extract). One or more polymerization inhibitors is added either to the liquefied solvent upstream of the extractor, or to the extract solution, or to the concentration equipment, to ensure that the extract contains inhibitors prior to concentration of the recovered carboxylic acid. The carboxylic acid is recovered and concentrated from the extract by boiling-off (evaporating) the propylene/propane solvent, which can be condensed and re-used (all, or in part) in the extraction step, or used as a raw material feed (in either vapor or condensed form) to the reactor in the process that generates the carboxylic acids. The concentration of the carboxylic acid may be carried out by means of one or more evaporators in series, or by means of distillation. The recovered carboxylic acid may be purified from the concentrate by means known to those skilled in the art of carboxylic acid processing; such means is outside the scope of the present invention.

The propylene and/or propane used as an extraction solvent in the present invention are much more volatile than either water or the propylene-oxidation reaction byproducts that may be present in the carboxylic acid extracts. They are also much more volatile than alternative carboxylic acid extraction solvents that have been described in the prior art. This high volatility affords several advantages:

The solvent can be readily separated from the carboxylic acid and other organics by simple evaporation or flash distillation; the solvent can be condensed and re-used in the extraction or in the reaction (that makes the carboxylic acids) without need of further purification. In contrast, some of the alternative solvents described in the prior art require complex fractional distillation or other means to separate and purify the solvent from the carboxylic acid or other reaction byproducts present in the extract.

The solvent can be boiled-off from the carboxylic acid at mild or even low/cryogenic temperatures. This minimizes the thermal exposure of the carboxylic acid during the concentration step. This is especially important when the carboxylic acid is AA, which tends to polymerize at high concentrations and/or elevated temperatures. Low-temperatures during concentration reduce the propensity to polymerize during processing, and allowing a reduction in the amount of AA polymerization inhibitors that needs to be added.

Low-temperature boil-off of the solvent allows the use of waste heat as the energy source to drive the separation, affording lower operating costs than if a conventional high-quality heat source (e.g. steam, hot oil, or electric heating) was used, as is required with low-volatility alternative solvents. If the evaporation is carried out at sub-ambient conditions, the cold solvent vapor and/or the carboxylic acid concentrate can be used (through suitable heat exchange means) to generate chilled cooling media (e.g. chilled water), in lieu of conventional energy and capital intensive mechanical refrigeration systems.

The carboxylic acid can be concentrated without being vaporized and re-condensed, as is required with solvents that are less volatile than carboxylic acid are employed. It is well known in the art of AA processing that condensation of AA vapors is prone to fouling due to polymerization: AA inhibitors are generally non-volatile; AA vapors are therefore un-inhibited, and when condensed, uninhibited AA can spontaneously polymerize. It is difficult to uniformly introduce inhibitors into the condensing (un-inhibited) AA. In contrast, when propylene and/or propane are used at the extraction solvent, AA inhibitors can be added to either the liquefied propylene/propane solvent prior to extraction, and/or to the AA-propylene/propane extract prior to the concentration step, and/or to the concentration equipment. Since AA is not vaporized, it remains in solution with the inhibitors throughout the concentration process, minimizing the likelihood of polymerization or fouling.

Propylene and/or propane are used as feedstocks for acrolein and AA manufacture, and typically are supplied to manufacturing facilities in pressurized, liquefied form. Thus, their use as extraction solvents in AA recovery eliminates the need to introduce, store, and handle additional materials, as would be required with solvents that are not "native" to acrolein and AA manufacture. Typical commercial grade propylene contains nominally 96 wt % propylene and 4 wt % propane.

The carboxylic acid extraction/concentration process using pressurized liquefied propylene/propane has the advantage of mechanical simplicity. Apart from liquid feed pumps and flow control valves, the process can, in principle, be designed with substantially no moving parts, relying on direct liquid-liquid contacting, heat transfer, pressure differences, and gravity flows to effect material transfers and separations.

In the recovery of carboxylic acids, especially acrylic acid (AA) from dilute aqueous mixtures by liquid-liquid extraction with a solvent comprising pressurized liquefied propylene and/or propane, in the extraction section, the majority of the carboxylic acid is transferred from the aqueous stream into the separate solvent phase. The carboxylic acid is then concentrated by evaporation or distillation, whereby the solvent is boiled away, leaving a concentrated solution of carboxylic acid, which may or may not contain water and/or other organic species that were co-extracted into the solvent. The extraction is carried out at a pressure exceeding the vapor pressure of the solvent at the highest temperature encountered in the extraction section, to ensure that the solvent remains liquefied throughout the extraction section. The carboxylic acid-lean aqueous raffinate can either be recycled, e.g. for absorption of additional carboxylic acid, or disposed and/or treated in an appropriate manner. The means by which the raffinate water is reused or treated is outside the scope of this invention. The ratio of solvent extractant to dilute aqueous mixture can range from about 0.5 to 1 to about 12 to 1 by weight.

The solvent removed from the extract in the concentration steps may be condensed and re-used for additional extraction, and/or used all or in part for other purposes, e.g. as feedstock for the reactions to produce the carboxylic acids or their precursors. If the condenser is elevated above the top of the extraction section, the (pressurized) condensed solvent can be recycled to the extraction section by gravity flow. The carboxylic acid can be purified from the concentrate by conventional means, e.g. those methods widely practiced in the commercial manufacture of high-purity products such as acrylic acid. The means for purifying the carboxylic acid from the concentrate are outside the scope of this invention.

Polymerization inhibitors, such as those known to those skilled in the art of AA purification, may be added to the liquefied solvent feed to the extractor, and/or to the carboxylic acid-solvent extract and/or at selected points in the concentration steps, to prevent the undesired polymerization of (unsaturated) carboxylic acids (such as AA) that can occur at high liquid concentrations or when subjected to heating.

The extraction and/or the concentration steps may be carried out as either batch or continuous operations.

The extraction is preferably carried out in a continuous counter-current liquid-liquid extractor column, configured to provide the equivalent of 3 or more theoretical stages of contacting.

The extractor column may be of any suitable configuration known to those skilled in the art of liquid-liquid extraction. However, due to the volatile and flammable nature of the propylene/propane solvent, it is most preferable to use an extraction column that does not have moving parts or seals for rotating or reciprocating equipment. It is also preferable to maintain the solvent as the dispersed phase in the extraction column, to minimize the inventory of flammable material. The extractor column is operated at elevated pressure, allowing the propylene and/or propane solvent to remain liquid at or above ambient temperatures, using solvent:aqueous feed ratios of 0.5:1-12:1 by weight, and preferably using solvent: aqueous feed ratios of 4:1-8:1 by weight.

The concentration of the carboxylic acid is achieved via evaporation of the solvent, preferably by a series of continuous evaporators, which may or may not be configured as multiple-effect evaporators in which the first stage evaporation takes place at substantially the same pressure as the extractor, and the evaporated solvent from the first evaporator is condensed at a physically elevated location, allowing the condensed propylene to return by gravity flow for recycle to extraction. It is preferable to carry out the extraction and first-stage evaporation at a pressure corresponding to the solvent boiling point. The temperature of the first-stage evaporation is preferably below about 50° C. and most preferably in that range of about 7° to 40° C. This allows for the use of waste heat sources to supply the energy for vaporization, and also allow for the use of near-ambient temperature cooling utilities (e.g. air or cooling water) to condense the vaporized propylene.

When polymerization inhibitors are used, it is preferable to use the class of inhibitors that do not require the presence of oxygen to be active, simplifying the inerting requirements to ensure that the propylene-containing vapors do not become flammable mixtures.

EXAMPLES

The following examples provide details wherein the carboxylic acid is acrylic acid (AA). However, while the subject invention is especially well suited for AA recovery and concentration using propylene as a solvent, it is not intended to limit its applicability to these materials. It should be apparent to those skilled in the art that the subject invention is applicable to other carboxylic acids, e.g. acetic acid, propionic acid, butyric acids, methacrylic acid, etc.

In the examples below, single-stage extractions were performed at ambient pressure by shaking dilute aqueous AA solutions (AAAS) with the solvent in a glass separator)/funnel, and then allowing the liquid phases to separate. The aqueous and organic layers were decanted and weighed. The two phases were analyzed to determine the AA extraction efficiency and the partitioning of the other organic species.

In the examples below, single-stage extractions were performed using a pressure-capable laboratory "shake test" apparatus. The procedure for the shake tests were:

1. Known amounts of aqueous acrylic acid solution (AAAS) and liquefied (pressurized) solvent were charged in two different pressure cylinders. The contents of the propylene cylinder were then transferred by gravity into the AAAS cylinder.
2. Once the AAAS cylinder was filled, it was placed in a shaker and shaken for 5 minutes.
3. After shaking, the cylinder containing the AAAS-solvent mixture was hung from a stand and left still to allow the liquid phases mixture to separate.
4. A section of heavy-wall transparent perfluoroalkoxy (PFA) fluoropolymer tubing was connected to the bottom of the mixture cylinder using tube fittings. The other end of the tubing was connected to a needle valve, which discharged into a laboratory glassware vacuum flask via an additional length of PFA tubing inserted through a rubber stopper.
5. The cylinder bottom valve was opened, filling the PFA connecting tube with the dense aqueous phase, which was visible in the transparent tubing.
6. Vacuum was continuously pulled on the flask. The needle valve was cracked-open, allowing liquid to transfer from the cylinder into the flask via the PFA tubing. Some foaming occurred in the flask, as dissolved solvent de-gases due to the letdown of pressure.
7. When a liquid/liquid interface was seen entering the PFA transfer line between the cylinder and the flask, the needle valve was closed, stopping the transfer.
8. Another flask was connected to the cylinder to recover the lower-density solvent-rich phase. When the solvent phase entered the flask, low-boiling solvent flashed-off, leaving behind in the flask the other organics.
9. The contents of both phases from the respective flasks were weighed. A (small) known amount of water and polymerization inhibitor were added to the flashed-off extract to prevent the concentrated AA from freezing (pure AA freezes at 55° F.) and to avoid any potential dimerization of AA. The two phases were analyzed to determine the AA extraction efficiency and the partitioning of the other organic species.

Examples 1-8

Single-Stage AA Extraction from Acrolein Process Wastewater Using Propylene as the Solvent An AAAS wastewater stream from an acrolein manufacturing process, containing the following (compositions given in weight %; the balance is water) was used.

| Acrylic Acid | 7.23% |
| Maleic acid | 1.05% |
| Acetic Acid | 1.36% |
| Allyl Alcohol | 0.07% |
| Acrolein | 0.06% |
| Acrolein dimer | 0.04% |

The solvent was commercial-grade propylene. Single-stage extractions were run using the "shake test" apparatus at ambient temperature and a pressure of approximately 220 psig. Eight propylene:Aqueous feed weight ratios were run, ranging from 0.82-6.08. The results are shown in Table 1 and plotted in FIG. 1. The above examples demonstrate the efficacy of using C3 hydrocarbons to extract carboxylic acid from aqueous streams.

TABLE 1

| Example | Propylene:Aqueous Feed Ratio | Average AA Recovery to Extract (%) |
| --- | --- | --- |
| 1 | 0.82 | 19 |
| 2 | 1.30 | 16 |
| 3 | 1.40 | 22 |
| 4 | 2.26 | 30 |
| 5 | 3.10 | 34 |
| 6 | 4.92 | 45 |
| 7 | 5.20 | 42 |
| 8 | 6.08 | 41 |

Examples 9-14

AA-Propylene-Water Liquid-Liquid Equilibria

An aqueous acrylic acid solution was prepared with laboratory-grade AA diluted to 5 or 10 weight % with distilled water. The solvent was commercial-grade propylene.

Figure 2:
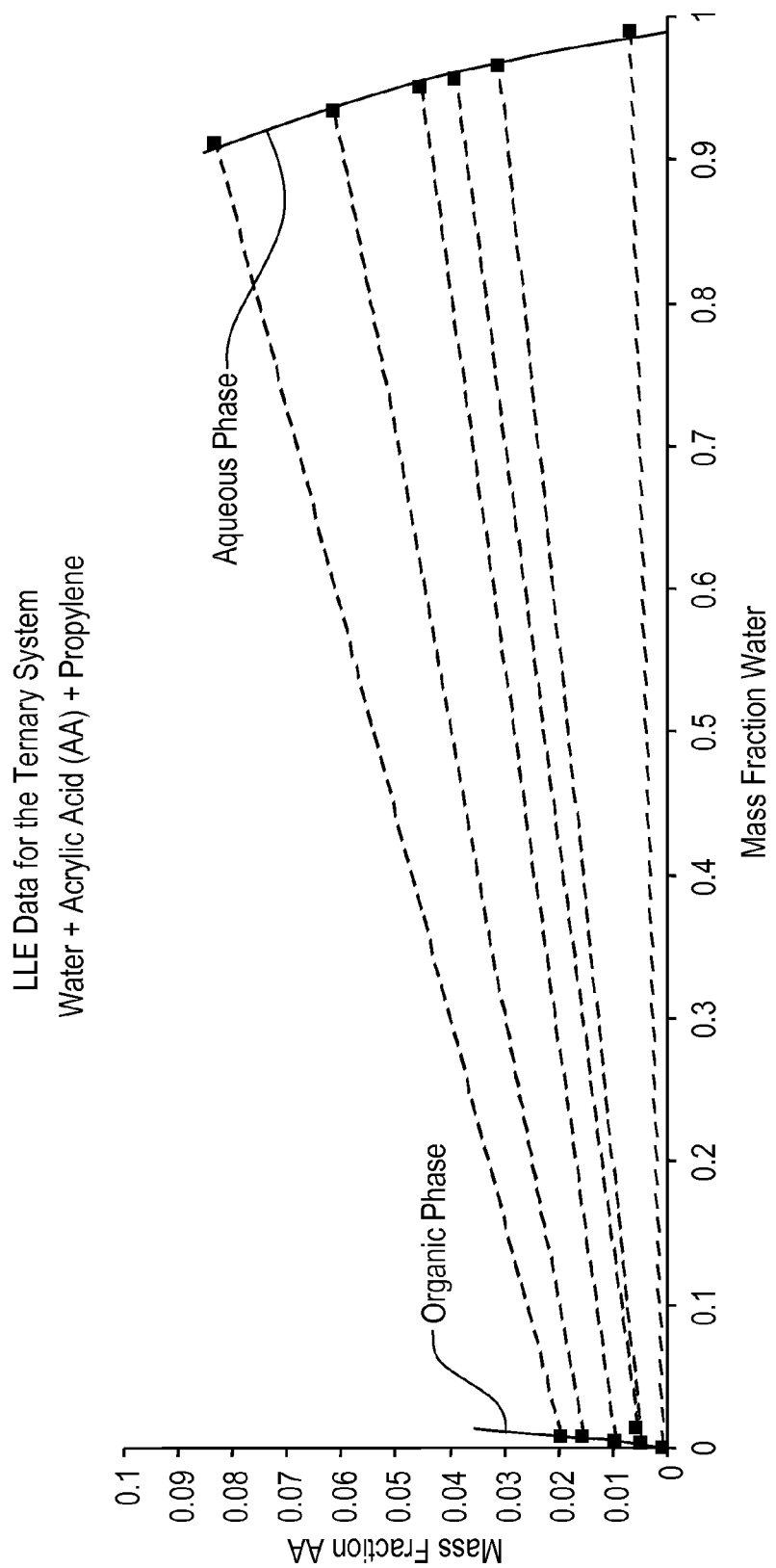
FIG. 2 is a plot of Mass fraction AA versus Mass fraction water for examples 1-15.

Single-stage extractions were run using the "shake test" apparatus at ambient temperature and a pressure of approximately 220 psig. Eight propylene:Aqueous feed mass ratios were run, ranging from 1:1-6.3:1. The partitioning of AA between the resulting 2 liquid phases and mass balances were determined. The results are shown in Table 2, and plotted in FIG. 2.

TABLE 2

| | Mass Fraction | | | | | | | | |
| --- | --- | --- | --- | --- | --- | --- | --- | --- | --- |
| | Feed Mixture | | | Organic Phase | | | Aqueous Phase | | |
| Example | AA | Water | Propylene | AA | Water | Propylene | AA | Water | Propylene |
| 9 | 0.015 | 0.135 | 0.850 | 0.010 | 0.005 | 0.985 | 0.046 | 0.952 | 0.003 |
| 10 | 0.010 | 0.182 | 0.809 | 0.005 | 0.005 | 0.990 | 0.031 | 0.966 | 0.003 |
| 11 | 0.002 | 0.149 | 0.850 | 0.001 | 0.002 | 0.997 | 0.007 | 0.991 | 0.002 |
| 12 | 0.051 | 0.461 | 0.488 | 0.019 | 0.009 | 0.971 | 0.083 | 0.913 | 0.004 |

TABLE 2-continued

| | Mass Fraction | | | | | | | | |
|---|---|---|---|---|---|---|---|---|---|
| | Feed Mixture | | | Organic Phase | | | Aqueous Phase | | |
| Example | AA | Water | Propylene | AA | Water | Propylene | AA | Water | Propylene |
| 13 | 0.016 | 0.309 | 0.675 | 0.006 | 0.014 | 0.980 | 0.039 | 0.958 | 0.003 |
| 14 | 0.027 | 0.252 | 0.720 | 0.016 | 0.009 | 0.976 | 0.062 | 0.935 | 0.003 |

Examples 9-14 demonstrate the preferential partitioning of AA into the C3 hydrocarbon phase when extracting AA from aqueous streams.

In examples 15-18, the process conditions and material balances were determined by computer simulation, using the Aspen Plus process simulator, with the non-random two-liquid (NRTL) thermodynamic model to calculate mixture properties, component separations, etc. The NRTL component binary pair parameters were based on values regressed from literature and experimental data, where available, and predicted using the Aspen "PCES" property component estimator (based on "UNIFAC" group contribution method) for binary pairs for which data was not available.

Example 15

Countercurrent Multi-stage AA Extraction from Acrolein Process Wastewater

The wastewater stream of Example 1 was contacted counter-currently with liquefied propylene containing 96 wt % propylene and 4 wt % propane in an extraction column providing several theoretical stages of contacting. The column operates with a top pressure of 15.31 atmospheres (225 psia).

The wastewater was fed to the top of the column, and the propylene solvent fed to the bottom of the column. The propylene-rich extract exited the top of the column, and the denser water-rich raffinate exited the bottom of the column.

The wastewater feed stream was at 100° F.; the liquefied propylene solvent feed temperature was 94° F.

Figure 3:
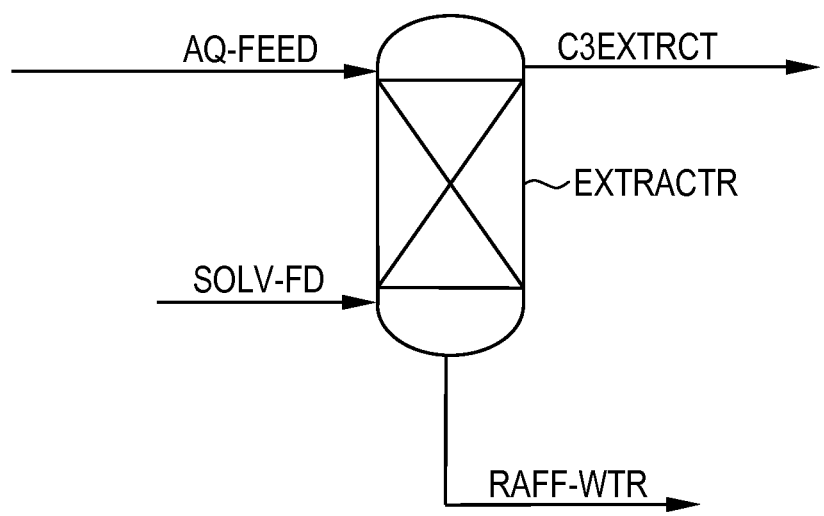
FIG. 3 is a process flow sheet for Example 15.
Figure 4:
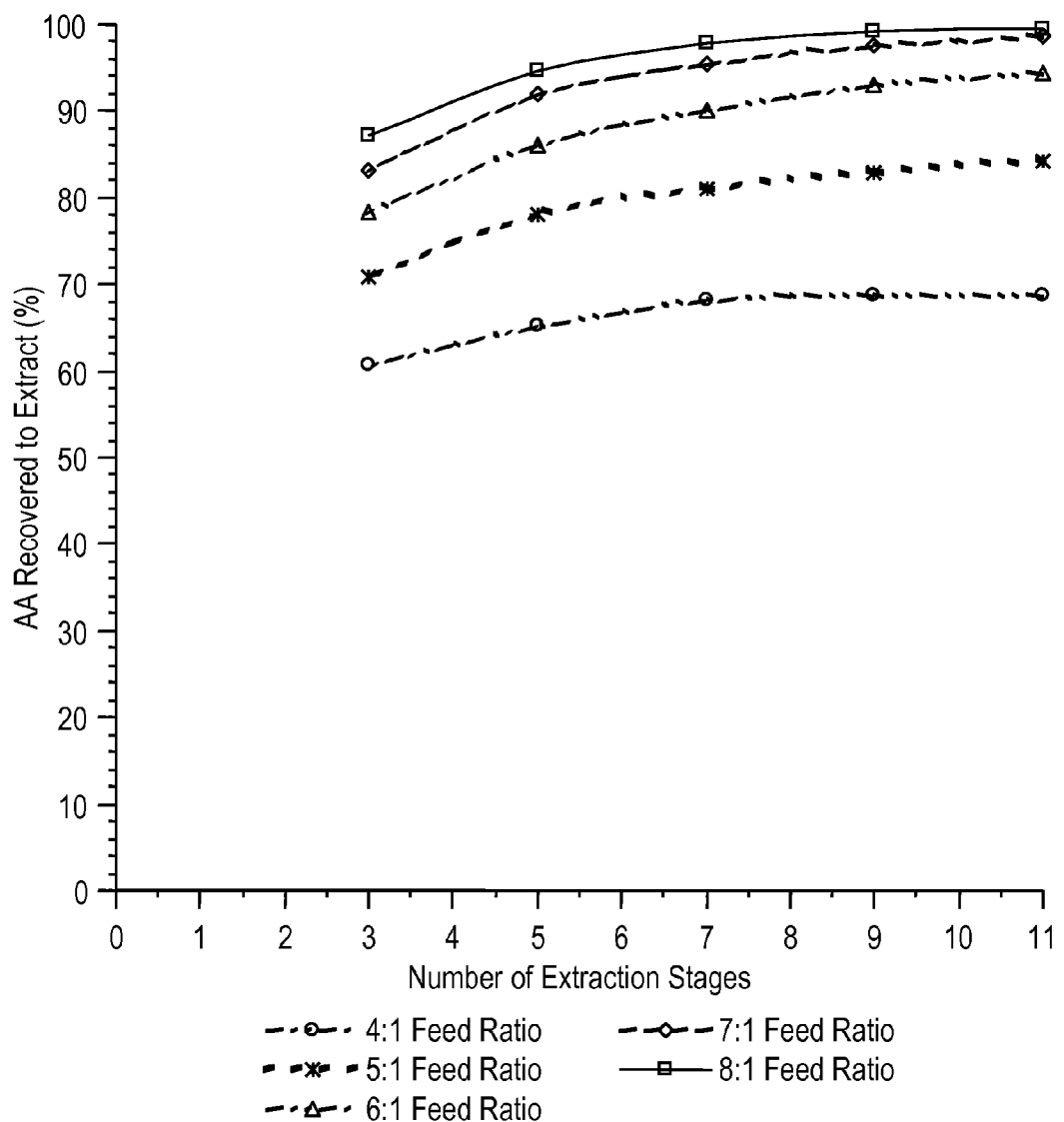
FIG. 4 is a plot of AA recovery versus Theoretical Extraction Stages for example 15.

The process flow sheet is depicted schematically in the FIG. 3. In the calculation, the number of theoretical extraction states was varied, from 3 to 11. The % recovery of acrylic acid (AA) extracted from the feed into the solvent extract vs. the number of theoretical extraction stages solvent feed ratio, for 4:1, 5:1, 6:1, 7:1, and 8:1 solvent:feed weight ratios, is shown in FIG. 4.

Example 15 demonstrates the practicality and efficacy of the present invention for efficiently recovering carboxylic acid from aqueous streams. Greater than 60% of the carboxylic acid can be recovered from a dilute aqueous feed containing less than 8 wt % carboxylic acid, with as few as 3 theoretical stages of counter-current contacting in the extractor, at solvent:aqueous feed ratios below 4:1. Extraction efficiencies exceeding 95% can be achieved by a combination of a modest increase in the number contacting stages and solvent ratios.

Example 16

AA Concentration by Flash Evaporation from the Propylene Extract

The waste-water stream of Example 1 was contacted counter-currently with a propylene-rich solvent, in an extraction column as described in Example 15, provided with the equivalent of 11 theoretical stages of contacting. The wastewater was fed to the top of the column, and the propylene solvent was fed to the bottom of the column. The propylene-rich extract exited the top of the column, and the denser water-rich raffinate exited the bottom of the column. A ratio of solvent:aqueous feed to the extractor of 6.1:1 by weight was used in the calculation.

Figure 5:
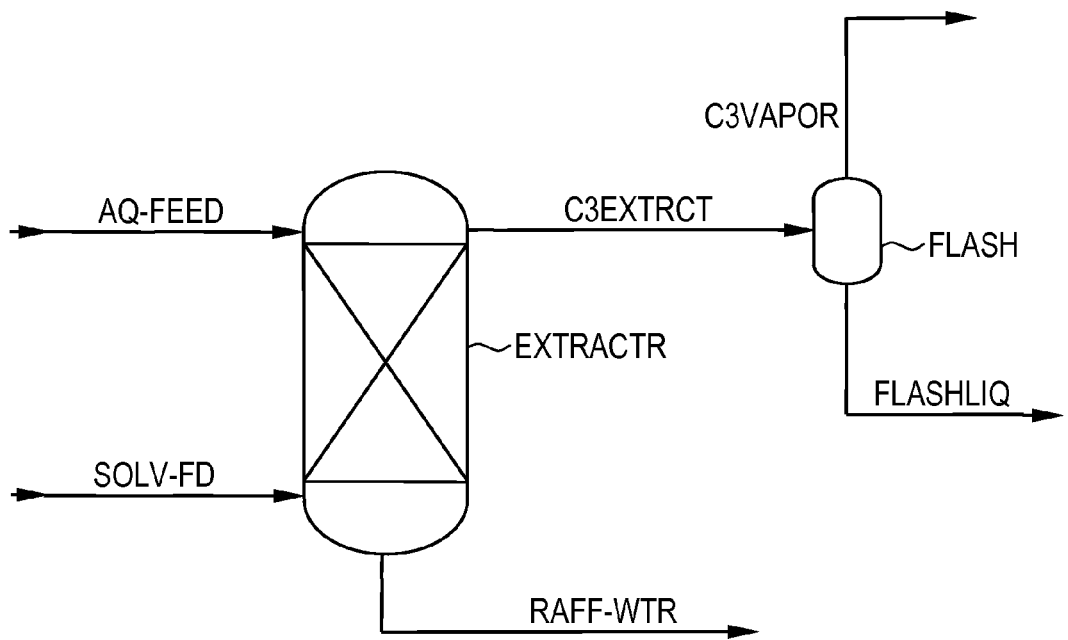
FIG. 5 is a process flow sheet for example 16.

The propylene extract of Example 15 was sent to a heated flash chamber, where the pressure was let-down to atmospheric pressure, with heating provided to maintain the effluent at 13° C. (55.4° F.) to keep the concentrate above the melting point of (pure) acrylic acid. The process flow sheet is depicted schematically in FIG. 5. The concentrated AA solution exiting the flash chamber would contain 91.7 wt % AA, 1.1% water, 2.0% propylene, with the balance being other organics compounds that co-extracted with the AA.

This example demonstrates the practicality and efficacy of the present invention for producing a concentrated carboxylic acid solution derived from a dilute aqueous stream. An acrylic acid concentration of greater than 90% can be achieved by a simple single-stage flash at mild temperatures. This is a higher concentration than is normally produced in AA manufacture, in the absorption of AA from the reactor effluent gases. If the concentrate of this example would be fed to an AA purification system, substantially less energy would be required to purify the AA compared to a conventional absorber effluent stream. The cooling effect of the vaporizing solvent at moderate temperature can also be used for process cooling, e.g. to produce chilled water.

Example 17

Countercurrent Multi-stage AA Extraction from Acrolein Process Wastewater, with Recycle of Solvent The wastewater stream of Example 1 was contacted counter-currently with a propylene-rich solvent, in an extraction column as described in Example 16, provided with the equivalent of 11 theoretical stages of contacting. The solvent comprised chemical-grade propylene required for feed to an acrolein production reactor, plus additional propylene that was recycled from concentration of acrylic acid recovered in the extract. The wastewater was fed to the top of the column, and the propylene solvent fed to the bottom of the column. The propylene-rich extract exited the top of the column, and the denser water-rich raffinate exited the bottom of the column.

Figure 6:
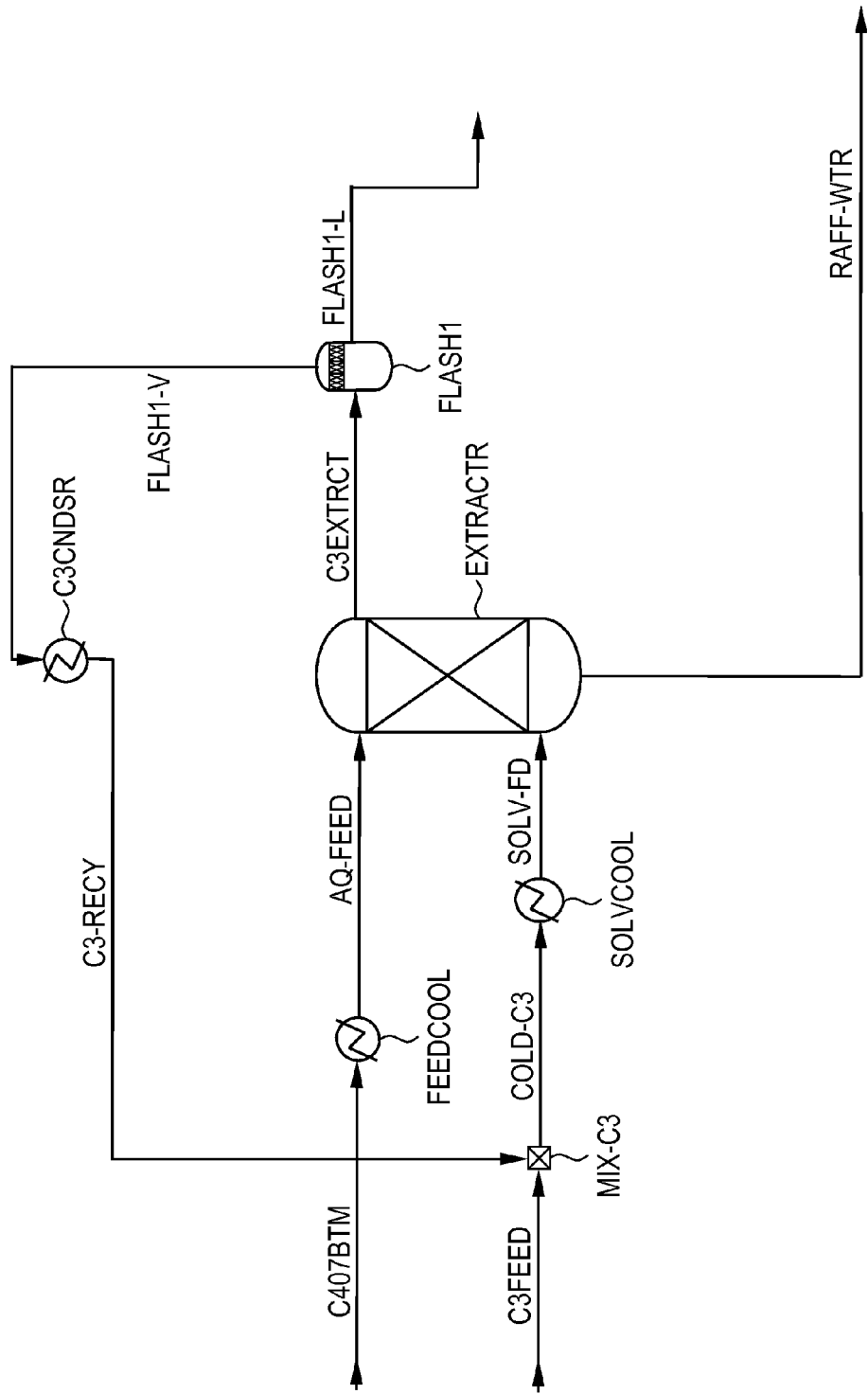
FIG. 6 is a process flow sheet for example 17.

The extract was sent to an evaporator, wherein the amount of solvent required for recycle to the solvent feed was evaporated-off from the extract, condensed, and combined with the make-up propylene feed. The liquid exiting the second evaporator contained the net propylene required for acrolein reaction, along with the recovered acrylic acid. The remaining propylene was separated from the acrylic acid in a downstream system. The process flow sheet is depicted schematically in the FIG. 6.

At these conditions, the partitioning of the components between the propylene extract and the aqueous raffinate is as follows:

|  | Extract | Raffinate |
|---|---|---|
| Acrylic Acid | 92.2% | 7.8% |
| Maleic Acid | 6.9% | 93.1% |
| Acetic Acid | 28.6% | 71.4% |
| Allyl Alcohol | 39.9% | 60.1% |
| Acrolein | 97.0% | 3.0% |
| Acrolein dimer | 99.3% | 0.7% |

The extract also contains 0.55 wt % water.

Example 17 demonstrates the practicality and efficacy of the present invention for efficiently recovering carboxylic acid from aqueous streams. Greater than 90% of the acrylic acid could be recovered from a dilute aqueous feed containing less than 8 wt % AA and less than 3% other organic impurities. Furthermore, it shows the surprising effect of selectivity for the desired acrylic acid, compared to the other organic acid and alcohol impurities present in the aqueous feed. Thus, the propylene extraction not only recovers the acrylic acid, but it also affords a degree of purification, which reduces the burden on any down-stream purification system.

Example 18

AA Concentration by Multi-stage Flash Evaporation from Propylene Extract, with Propylene Recycled to Extraction In this example, the extractor is configured as in Example 17. The propylene extract was sent to a heated flash chamber, with the pressure maintained at substantially the same as the extractor top pressure. The first flash chamber was provided with sufficient heat to vaporize approximately 90% of the propylene solvent, i.e. approximately 5.5 kg of propylene per kg of wastewater from Example 1. The first stage vaporizer operated at approximately 40 deg C. (104 deg F.).

The vaporized propylene from the first stage vaporizer was condensed and recycled by gravity flow, where it was mixed with make-up liquid propylene, for use as the solvent feed to extraction.

The liquid effluent from the first evaporator was sent to a second evaporator, where the pressure was let-down to approximately 2 atmospheres (40 psia), with heating provided to maintain the effluent at or above 7° C. (45° F.), to keep the liquid (crude AA with some residual propylene) above its freezing point. Some water may be added to the crude AA, to further suppress its freezing point (the minimum freezing point for aqueous AA mixtures is realized at approximately 30 wt % water in AA). The vaporized propylene from the second vaporizer was used as feed to an acrolein reactor. The cooling effect of the vaporizing propylene in the second stage evaporator was used in lieu of mechanical refrigeration, to produce chilled water, for use elsewhere in the process.

The concentrated AA solution exiting the second-stage evaporator was flashed to atmospheric pressure, to vent-off residual dissolved propylene. The flash drum was maintained above the freezing point of the AA concentrate (pure AA freezes at 13° C.; 30% AA freezes at −11° C.). The AA concentrate may be transported to an AA manufacturing facility for final purification of the recovered AA.

The raffinate water exiting the extractor was flashed adiabatically to atmospheric pressure, to vent-off any residual propylene, prior to sending the AA-depleted water to waste treatment.

Figure 7:
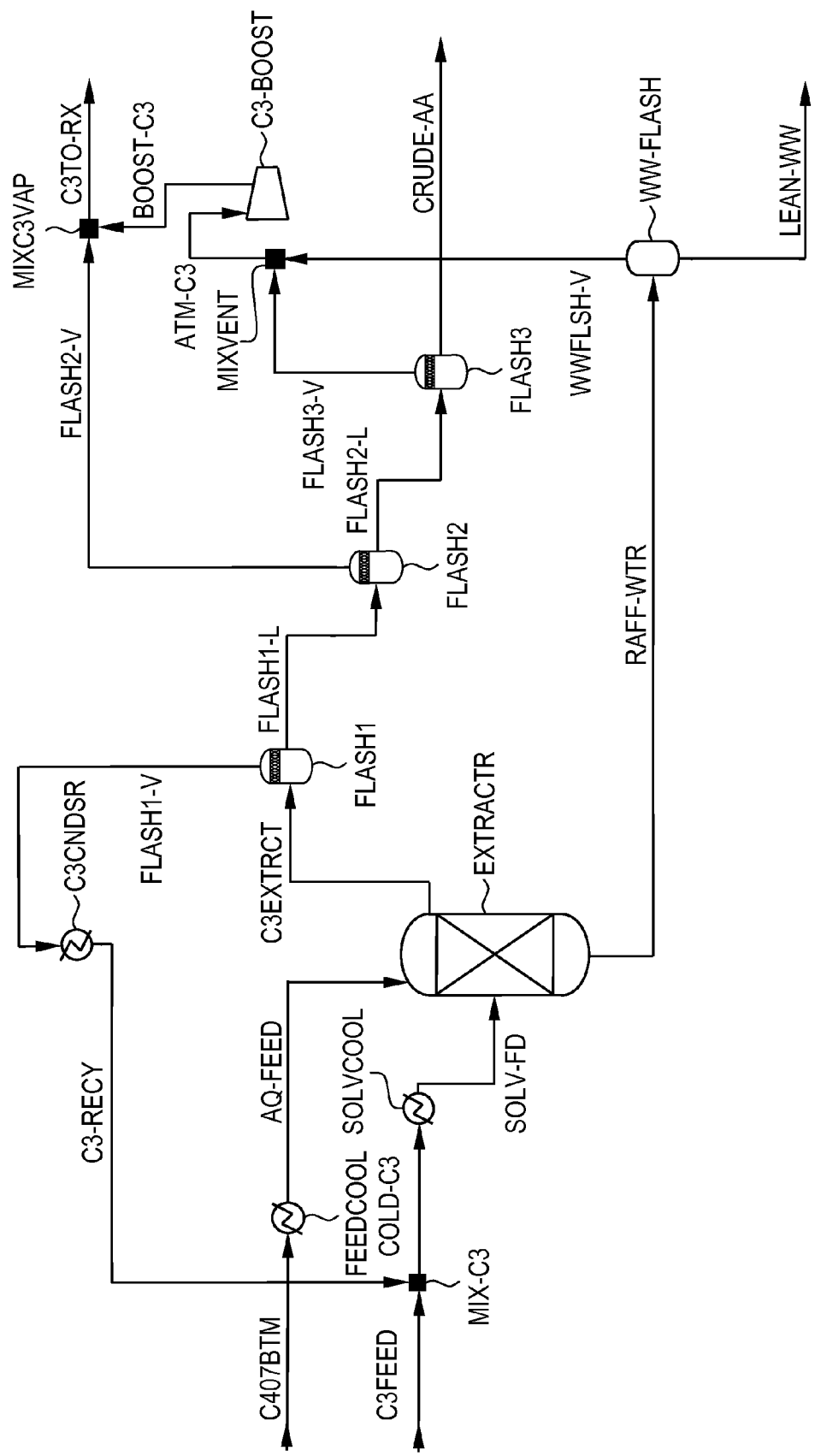
FIG. 7 is a process flow sheet for example 18.

The propylene vented from the atmospheric flash of the AA concentrate and the aqueous raffinate was collected and recycled to the acrolein process, i.e. boosted to the reactor feed pressure e.g., by a blower or jet ejector blower, or alternatively, used as a fuel stream. The process flow sheet is depicted schematically in the FIG. 7.

Without dilution water in the second-stage evaporation, the concentrated AA solution exiting the final flash chamber would contain 90.9 wt % AA, 0.4 wt % water, with the balance being other organic compounds that co-extracted with the AA.

This example demonstrates the practicality and efficacy of the present invention for integrating the propylene used for acrolein manufacture, with recovery of a concentrated acrylic acid solution, which is an item of commerce, from a process wastewater stream. The concentrated AA is at a higher concentration and comparable impurities profile to the crude AA in the absorber effluent typically produced in AA manufacture. Hence, the recovered AA concentrate may be combined with the normal crude AA, with a beneficial impact on the energy required for AA purification due to the lower water content.

While the present invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

The invention claimed is:

1. A method for separating mono carboxylic acids and/or aldehydes selected from the group consisting of acrylic acid, acetic acid, propionic acid, butyric acids, methacrylic acid, acrolein, acetaldehyde, methacrolein, propionaldehyde, butyraldehyde, crotonaldehyde, 3-butenal, and mixtures thereof from aqueous solutions by extraction wherein the improvement comprises:
   a liquid-liquid extraction of said mono carboxylic acid and/or aldehyde using propylene and/or propane extractant in the liquid phase, and
   recovering said carboxylic acids and/or aldehydes as a concentrate by evaporating the propylene and/or propane extractant at temperatures between about 7° and 40° C. and at pressures wherein said carboxylic acid and/or aldehydes remain in the liquid state.

2. The method of claim 1 wherein said extractant comprises about 96 wt % propylene and 4 wt % propane.

3. The method of claim 1 further comprising adding polymerization inhibitors to the propylene and/or propane extractant.

4. The method of claim 1 wherein said aqueous solution comprises less than about 10% by weight of said carboxylic acids and/or aldehydes.

5. The method of claim 1 wherein said extractant to aqueous solution ratio is from about 0.5 to 1 to about 12 to 1 by weight.

6. The process of claim 1 where the recovering said carboxylic acids and/or aldehydes as a concentrate by evaporating is carried out using multiple-effect evaporators operating at progressively lower pressures.

7. The process of claim 1 further comprising condensation and recycling of said propylene and/or propane extractant to said liquid-liquid extraction after said recovering said carboxylic acids and/or aldehydes as a concentrate by evaporating.

8. The processes of claims 1 wherein the heat for said recovering said carboxylic acids and/or aldehydes as a concentrate by evaporating is provided by indirect contact with warm coolant media to produce chilled coolant.

* * * * *

UNITED STATES PATENT AND TRADEMARK OFFICE
CERTIFICATE OF CORRECTION

| | | |
|---|---|---|
| PATENT NO. | : 9,156,769 B2 | Page 1 of 1 |
| APPLICATION NO. | : 14/222967 | |
| DATED | : October 13, 2015 | |
| INVENTOR(S) | : S. Schon et al. | |

It is certified that error appears in the above-identified patent and that said Letters Patent is hereby corrected as shown below:

Title page

Item (12), delete "Schon" and insert --Schon et al.--

Item (72), Inventors: insert the following inventor: --Cecile V. Bertrand, Bagnois (FR)--

Signed and Sealed this
Seventh Day of June, 2016

Michelle K. Lee
*Director of the United States Patent and Trademark Office*